United States Patent [19]
Yuasa et al.

[11] 4,374,272
[45] Feb. 15, 1983

[54] PROCESS FOR PREPARING 2-(4'-HYDROXYARYL)-2-(4'-AMINOARYL)-PROPANES

[75] Inventors: Teruo Yuasa; Noboru Yamazaki, both of Nagoya; Yoshio Morimoto, Tokai, all of Japan

[73] Assignee: Mitsui Toatsu Chemicals, Inc., Tokyo, Japan

[21] Appl. No.: 92,175

[22] Filed: Nov. 7, 1979

[30] Foreign Application Priority Data

Nov. 8, 1978 [JP] Japan .................. 53-137528

[51] Int. Cl.³ .............................................. C07C 87/64
[52] U.S. Cl. .................. 564/315; 260/465 E; 560/1
[58] Field of Search ........... 260/570 R, 570 D, 465 E; 564/315

[56] References Cited

U.S. PATENT DOCUMENTS 3,311,660  3/1967 Krimm et al. .................. 260/570
3,418,371 12/1968 Krimm et al. .................. 260/570
3,496,239  2/1970 Hamilton et al. ............. 260/570 X

FOREIGN PATENT DOCUMENTS 1251334 10/1967 Fed. Rep. of Germany ...... 260/570

Primary Examiner—Robert V. Hines
Attorney, Agent, or Firm—Fisher, Christen & Sabol

[57] ABSTRACT

A process for preparing 2-(4'-hydroxyaryl)-2-(4'-aminoaryl)-propanes of the general formula

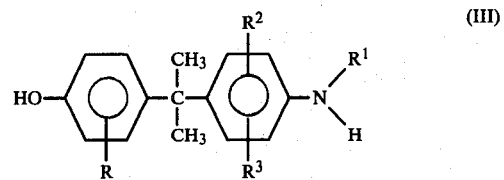

wherein R represents a hydrogen or halogen atom or an alkyl, aryl, nitro, nitrile, acyl, acyloxy or amino group, $R^1$ represents a hydrogen atom or an alkyl group having 1 to 4 carbon atoms, and $R^2$ and $R^3$, independently from each other, represent a hydrogen or halogen atom, a nitro group or an alkyl group having 1 to 4 carbon atoms, which comprises reacting (A) at least one isopropenyl phenol compound selected from the group consisting of isopropenyl phenol derivatives of the general formula

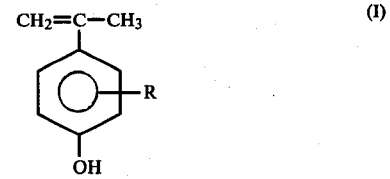

wherein R is as defined,
and di- to eicosa-mers of said isopropenyl phenol derivatives with (B) an aromatic amine of the general formula

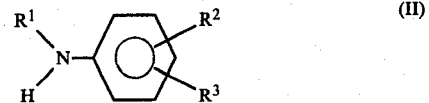

wherein $R^1$, $R^2$ and $R^3$ are as defined,
in the presence of 0.00001 to 0.008 mole, per mole of said isopropenylphenol compound (A) calculated as a monomer, of a acid catalyst and in the presence or absence of a phenolic solvent.

10 Claims, No Drawings

PROCESS FOR PREPARING 2-(4'-HYDROXYARYL)-2-(4'-AMINOARYL)-PROPANES

This invention relates to a novel process for preparing 2-(4'-hydroxyaryl)-2-(4'-aminoaryl-propanes.

Heretofore, 2-(4'-hydroxyaryl)-2-(4'-aminoaryl)-propanes have been produced usually by reacting isopropenyl phenol derivatives or dimers thereof with aromatic amines in the presence of 0.01 to 1.0 mole, per mole of the isopropenylphenol derivatives or dimers thereof, of an acid catalyst, as described, for example, in Belgian Pat. No. 633,236. This conventional method, however, has the defect that the yield of the 2-(4'-hydroxyaryl)-2-(4'-aminoaryl)-propanes is not as high as is satisfactory, and many difficulties are encountered in producing the starting pure isopropenyl phenol derivatives industrially.

It is an object of this invention therefore to provide 2-(4'-hydroxyaryl)-2-(4'-aminoaryl)-propanes at low cost by discovering a process which can eliminate these defects of the prior art.

According to this invention, this object can be achieved by a process for preparing 2-(4'-hydroxyaryl)-2-(4'-aminoaryl)-propanes of the general formula

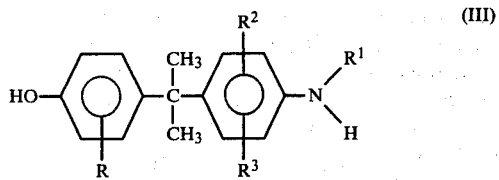

(III)

wherein R represents a hydrogen or halogen atom or an alkyl, aryl, nitro, nitrile, acyl, acyloxy or amino group, $R^1$ represents a hydrogen atom or an alkyl group having 1 to 4 carbon atoms, and $R^2$ and $R^3$, independently from each other, represent a hydrogen or halogen atom, a nitro group or an alkyl group having 1 to 4 carbon atoms, which comprises reacting (A) at least one isopropenyl phenol compound selected from the group consisting of isopropenyl phenol derivatives of the general formula

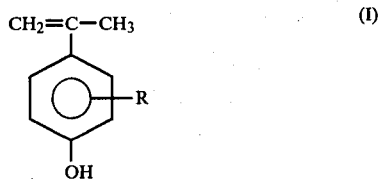

(I)

wherein R is as defined,
and di- to eicosa-mers of said isopropenyl phenol derivatives with (B) an aromatic amine of the general formula

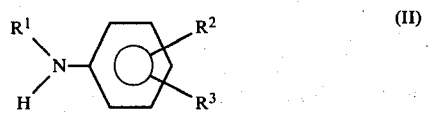

(II)

wherein $R^1$, $R^2$ and $R^3$ are as defined,
in the presence of 0.00001 to 0.008 mole, per mole of said isopropenylphenol compound (A) calculated as a monomer, of an acid catalyst and in the presence or absence of a phenolic solvent.

The di- to eicosa-mers of the isopropenyl phenol derivatives of formula [I] are polymers represented by the general formula

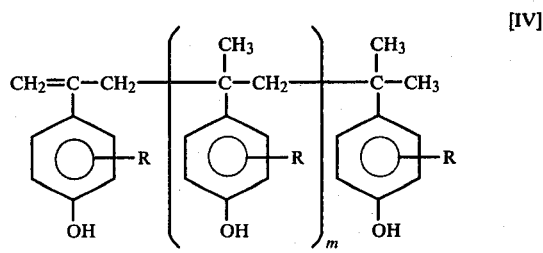

[IV]

wherein R is as defined, and m is 0 or an integer of 1 to 18, or

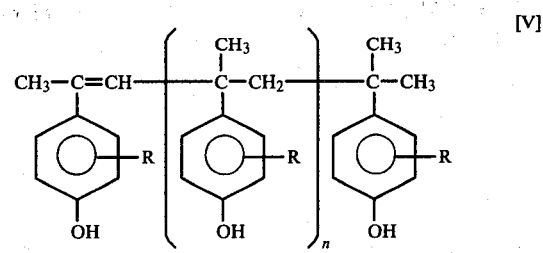

[V]

wherein R is as defined, and n is 0 or an integer of 1 to 18.

These polymers can be obtained as a mixture of polymers having various degrees of polymerization by polymerizing the isopropenyl phenol derivatives of formula [I] in a known manner. For example, heating isopropenyl phenol in the presence or absence of an acid yields a mixture of 2,4-bis(4'-hydroxyphenyl)-4-methyl-pentene-1 (to be referred to as dimer [IV]) corresponding to formula [IV] in which m is zero and 2,4-bis(4'-hydroxyphenyl)-4-methyl-pentene-2 (to be referred to as dimer [V]) corresponding to formula [V] in which n is zero. When the heating is performed for a relatively long period, the mixture obtained contains a larger proportion of the dimer [V]. By selecting the polymerization conditions, a mixture consisting of 90% of the dimer [IV] and 10% of the dimer [V] can be obtained, and recrystallization of this mixture from a mixture of benzene and methanol affords dimer [IV] of high purity. The dimer [IV] used in Examples 2 and 3 given hereinbelow is of high purity obtained in this manner.

Advantageously, the process of this invention is carried out in the presence of a phenol, because it accelerates the reaction of forming the desired product.

Heretofore, the isopropenyl phenol derivative [I] has generally been produced by isolation from a mixture of an isopropenyl phenol derivative and a phenol which is obtained by the catalytic decomposition of a dihydroxydiaryl propane. Since the process of this invention can be conveniently carried out in the presence of phenols as described above, the aforesaid mixture of the isopropenyl phenol derivative and phenol can be directly used as a starting material without isolating the isopropenyl phenol derivative. This brings about a great industrial advantage.

Specific examples of the isopropenyl phenol compound (A), i.e. the isopropenyl phenol derivatives of formula [I] and the di- to eicosa-mers thereof, that can be used in the process of this invention include:

p-isopropenyl phenol, 2,4-bis(4'-hydroxyphenyl)-4-methyl-pentene-1 of the formula

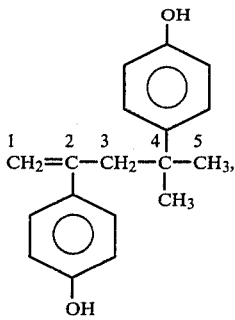

2,4-bis(4'-hydroxyphenyl)-4-methyl-pentene-2 of the formula

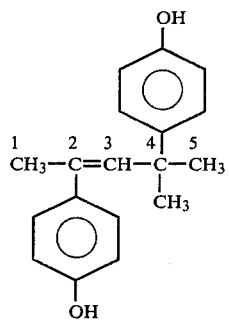

and linear tri- to eicosa-mers of p-isopropenyl phenol. In the present invention, these isopropenyl phenol compounds are used either singly or as a mixture of two or more.

Examples of the aromatic amine (B) of general formula [II] that can be used in this invention include aniline, o-chloroaniline, 2,5-dichloroaniline, o-nitroaniline, o-toluidine, 2,6-xylidine, o-isopropylaniline, N-methylaniline, o-aminophenol, and diphenylamine.

There is no particular restriction on the ratio between the isopropenyl phenol compound (A) and the aromatic amine (B) used in the process of this invention. The suitable amount of the aromatic amine is 1.0 to 2.0 moles per mole of the isopropenyl phenol compound (calculated as a monomer). Use of a larger proportion of the aromatic amine should desirably be avoided because it will complicate the post-treatment procedure.

The acid catalyst used in this invention includes, for example, protonic acids such as hydrochloric acid, sulfuric acid, phosphoric acid, chloroacetic acid, toluenesulfonic acid, methanesulfonic acid and oxalic acid; Lewis acids such as aluminum chloride, tin tetrachloride and boron trifluorides; and solid acids such as cation exchange resins. These acids may be used singly or as a mixture of two or more. The amount of the acid catalyst may be as small as 0.00001 to 0.008 mole, preferably 0.00005 to 0.005 mole, per mole of the isopropenyl phenol compound (A) (calculated as a monomer). This is another industrial advantage of the present invention because it means that there is no need to use a large amount of acids as in the prior art, and therefore, a neutralizing operation after the reaction is unnecessary or can be drastically simplified. The acid is used preferably in the form of a 5–50% aqueous solution, a salt with the aromatic amine, or a complex with the aromatic amine.

The reaction is completed usually in 0.5 to 10 hours, preferably 1 to 5 hours, at a temperature of 80° to 250° C., preferably 150° to 180° C.

If desired, the process of this invention can be carried out in a solvent such as an aromatic hydrocarbon, chlorinated hydrocarbon, ether, ester, alcohol or phenol. The presence of phenols as a solvent is very advantageous because the reaction of forming the desired product can be accelerated. Examples of the phenols are phenol, cresol, xylenol, propylphenol, butylphenol, amylphenol, octylphenol, and nonylphenol. In one embodiment of using the phenol in this way, the mixture of isopropenyl phenol compound and phenol obtained by the catalytic decomposition of a dihydroxydiaryl propane may be directly used in the reaction. The amount of the phenol used is generally not more than 20 moles per mole of the isopropenyl phenol compound (A) (calculated as a monomer). Use of the phenol in an amount of 0.5 to 2 moles is preferred because it makes the reaction proceed smoothly, and renders the reaction operation easy.

The 2-(4'-hydroxyaryl)-2-(4'-aminoaryl)-propanes produced by the process of this invention can be used as antioxidants, stabilizers, raw materials for polymeric compounds, and intermediates for dyes, pigments, agricultural chemicals, pharmaceuticals, etc.

The following non-limitative Examples specifically illustrate the present invention. All percentages in these examples are by weight.

EXAMPLE 1

A mixture of 13.4 g (0.1 mole) of p-isopropenyl phenol monomer and 18.6 g (0.2 mole) of aniline was stirred at 150° C. To the mixture was added 0.50 g of a solution obtained by adding 1.28 g of 35% hydrochloric acid to 93 g of aniline and stirring the mixture well (to be referred to as a catalyst solution) (0.0018 mole of catalyst per mole of p-isopropenyl phenol), and the reaction was carried out for 3 hours. Gas-chromatographic analysis of the reaction mixture showed that 21.3 g (yield 94%) of 2-(4'-hydroxyphenyl)-2-(4'-aminophenyl)-propane of the formula

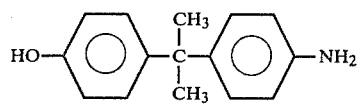

was formed.

EXAMPLE 2

A mixture of 13.4 g of phenol, 13.4 g of 4-methyl-2,4-bis(4'-hydroxyphenyl)-pentene-1 (linear dimer [IV] of p-isopropenyl phenol) and 18.6 g of aniline was stirred at 150° C. (2 moles of the aniline per mole of the monomer calculated). To the mixture was added 0.52 g of the catalyst solution prepared in Example 1 (0.0019 mole of catalyst per mole of the monomer calculated), and the reaction was carried out for 3 hours. Gas-chromatographic analysis of the reaction mixture showed that 0.23 g of bisphenol A and 21.9 g (yield 97%) of 2-(4'- hydroxyphenyl)-2-(4'-aminophenyl)-propane were formed.

EXAMPLE 3

Example 2 was repeated except that 9.3 g of aniline (1 mole of aniline per mole of the monomer calculated) was used. After reaction for 3 hours at 150° C., the reaction mixture was analyzed by gas-chromatography. It was found that 0.5 g of bisphenol A, and 21.5 g (yield 95%) of 2-(4'-hydroxyphenyl)-2-(4'-aminophenyl)-propane were formed.

EXAMPLE 4

Ten grams of aniline was added to a mixture consisting of 13.0 g of phenol, 3.4 g of p-isopropenyl phenol monomer, 8.5 g of a linear dimer of p-isopropenyl phenol, 1.1 g of a linear trimer of p-isopropenyl phenol and 0.8 g of a linear tetramer and higher polymers of p-isopropenyl phenol (1.05 mole of aniline per mole of the p-isopropenyl phenol monomeric unit). The mixture was stirred at 180° C. Then, 0.2 g of 10% hydrochloric acid (0.0053 mole per mole of the p-isopropenyl phenol monomeric unit) was added, and the reaction was performed for 2 hours. Gas-chromatographic analysis of the reaction mixture showed that 0.38 g of bisphenol A and 21.8 g (yield 93%) of 2-(4'-hydroxyphenyl)-2-(4'-aminophenyl)-propane were formed.

EXAMPLE 5

Aniline (175 g) and 200 g of a mixture consisting of 2.5% of p-isopropenyl phenol monomer, 72% of a linear dimer of p-isopropenyl phenol, 4.3% of a linear trimer of p-isopropenyl phenol, 2.1% of a linear tetramer of p-isopropenyl phenol, 0.9% of a linear pentamer of p-isopropenyl phenol, 1.5% of a linear hexamer and higher polymers of p-isopropenyl phenol, and 16.7% of other compounds were stirred at 150° C. (1.52 moles of aniline per mole of the p-isopropenyl phenol monomeric unit). Then, 3 g of 10% hydrochloric acid (0.0066 mole per mole of the p-isopropenyl phenol monomeric unit) was added, and the reaction was performed at 150° C. for 2 hours. With stirring, the reaction mixture was cooled to room temperature, and the precipitate was collected. Washing of the precipitate with benzene afforded 258 g of pale brown crystals. Recrystallization of the resulting crude crystals from methanol/acetone afforded white crystals of 2-(4'-hydroxyphenyl)-2-(4'-aminophenyl)-propane having a melting point of 191.5° C. in a yield of 92%.

EXAMPLE 6

N-methylaniline (20 g) was added to 50 g of a mixture of alkenyl phenols and phenol obtained by the alkali cleavage of bisphenol A (consisting of 47.7% of phenol, 1.4% of p-isopropyl phenol, 1.1% of bisphenol A, 21.4% of p-isopropyl phenol monomer, 4.8% of a linear dimer of p-isopropenyl phenol, 4.4% of a linear trimer and higher polymers of p-isopropenyl phenol, and 19.2% of other compounds) (1.62 moles of N-methylaniline per mole of the p-isopropenyl phenol monomeric unit). The mixture was stirred at 170° C. Then, 0.8 g of the catalyst solution prepared in Example 1 (0.0026 mole of catalyst per mole of the p-isopropenyl phenol monomeric unit) was added, and the reaction was performed for 3 hours. Gas-chromatographic analysis of the reaction mixture showed that 0.98 g of bisphenol A and 25.4 g (yield 92%) of 2-(4'-hydroxyphenyl)-2-(4'-methylaminophenyl)-propane having a melting point of 135.5° to 137° C. were formed.

EXAMPLE 7

Aniline (350 g) and 1 kg of a mixture of alkenyl phenols and phenol obtained by the alkali cleavage of bisphenol A (consisting of 48.9% of phenol, 1.4% of p-isopropyl phenol, 1.2% of bisphenol A, 0.3% of p-isopropenyl phenol monomer, 35.1% of a linear dimer of p-isopropenyl phenol, 3.5% of a linear trimer and higher polymers of p-isopropenyl phenol, and 9.6% of other compounds) were stirred at 170° C. (1.30 moles of aniline per mole of the p-isopropenyl phenol monomeric unit). Then, 7.8 g of the catalyst solution prepared in Example 1 (0.0010 mole of catalyst per mole of the p-isopropenyl phenol monomeric unit) was added, and the reaction was performed for 3 hours. After the reaction, the reaction mixture was allowed to cool while it was stirred at room temperature. When it was cooled to about 80° C., 500 g of toluene was added, and the mixture was well stirred. The precipitate was collected by filtration to afford 600 g (yield 91%) of crude crystals of the desired 2-(4'-hydroxyphenyl)-2-(4'-aminophenyl)-propane.

EXAMPLE 8

The same reaction as in Example 7 was performed. After the reaction, phenol and the excess of aniline were distilled off under reduced pressure to form 750 g of a residue. Methanol (1 kg) was added to the solid residue, and the product was finely ground. The ground product was collected by filtration to afford 612 g (yield 93%) of 2-(4'-hydroxyphenyl)-2-(4'-aminophenyl)-propane.

EXAMPLE 9

The same reaction as in Example 7 was performed. The reaction mixture was boiled with 2 liters of methanol, and cooled to separate 515 g of crystals having a melting point of 189° to 190° C. The solvent, phenol and aniline were evaporated from the mother liquor, and then methylene chloride were added. Filtration of the mixture afforded additional 80 g (yield 90%) of 2-(4'-hydroxyphenyl)-2-(4'-aminophenyl)-propane as crystals.

EXAMPLE 10

Aniline (25 g; 1.39 moles of aniline per mole of p-isopropenyl-o-cresol) was added to 50 g of a mixture of o-cresol and p-isopropenyl-o-cresol (1:1 mole ratio) obtained by the alkali cleavage of 2,2-bis(4'-hydroxy-3'-methylphenyl)-propane. The mixture was stirred at 170° C., and 1.5 g of the catalyst solution prepared in Example 1 (0.0029 mole of catalyst per mole of p-isopropenyl-o-cresol) was added. The reaction was performed for 3 hours. Gas-chromatographic analysis of the resulting reaction mixture showed that 42.7 g (yield 91%) of 2-(4'-hydroxy-3'-methylphenyl)-2-(4'-aminophenyl)-propane having a melting point of 152.5 to 153.5° C. was formed.

COMPARATIVE EXAMPLE 1

Aniline (83.7 g) and 26.8 g of a linear dimer of p-isopropenyl phenol were stirred at 150° C. (5.0 moles of aniline per mole of the p-isopropenyl phenol monomeric unit). Then, 13.0 g of the catalyst solution prepared in Example 1 (0.5 mole of catalyst per mole of the p-isopropenyl phenol monomeric unit) was added, and the reaction was performed for 3 hours. After the reaction, the reaction mixture was analyzed by gas-chromatography. It was found that 29.5 g (yield 65%) of 2-(4'-hydroxyphenyl)-2-(4'-aminophenyl)-propane was formed. Analysis by high-speed liquid chromatography showed that about 14 g of high-molecular-weight substances were formed.

EXAMPLE 11

Aniline (18.6 g) and 34.4 g of the same mixture of alkenylphenols and phenol as used in Example 7 were stirred at 150° C. (2 moles of aniline per mole of the p-isopropenyl phenol monomeric unit). Then, 0.0065 g of aniline hydrochloride (0.0005 mole of catalyst per mole of the p-isopropenyl phenol monomeric unit) was added as a catalyst, and the reaction was performed for 3 hours. After the reaction, the reaction mixture was analyzed by gas chromatography. It was found that 19.7 g (yield 87%) of 2-(4'-hydroxyphenyl)-2-(4'-aminophenyl)-propane and 0.24 g of bisphenol A were formed.

COMPARATIVE EXAMPLE 2

Example 11 was repeated except that the amount of the aniline hydrochloride was changed to 0.26 g (0.02 mole of catalyst per mole of the p-isopropenyl phenol monomeric unit). After the reaction, the reaction mixture was analyzed by gas chromatography. It was found that 17.3 g (yield 76%) of 2-(4'-hydroxyphenyl)-2-(4'-aminophenyl)-propane and 1.4 g of bisphenol A were formed.

What we claim is:

1. A process for preparing 2-(4'-hydroxyaryl)-2-(4'-aminoaryl)-propanes comprising reacting
    (A) at least one isopropenyl phenol compound selected from the group consisting of isopropenyl phenol derivatives of the formula:

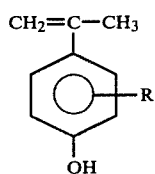

wherein R represents a hydrogen or halogen atom or an alkyl, aryl, nitro, nitrile, acyl, acyloxy or amino group, and di- to eicosa-mers of said isopropenyl phenol derivatives with
    (B) an aromatic amine selected from the group consisting of aniline, o-chloroaniline, 2,5-dichloroaniline, o-nitroaniline, o-toluidine, 2,6-xylidine, o-isopropylaniline, N-methylaniline, o-aminophenol, and diphenylamine, in the presence of 0.00001 to 0.008 mole, per mole of said isopropenylphenol compound (A) calculated as a monomer, of an acid catalyst, wherein the amount of the aromatic amine (B) is 1.0 to 2.0 moles per mole of the isopropenyl phenol compound (A) calculated as a monomer.

2. A process as claimed in claim 1 wherein R is a hydrogen atom or a methyl group.

3. A process as claimed in claim 1 or 2 wherein said reaction is carried out in the presence of a phenolic solvent.

4. A process as claimed in claim 3 wherein said phenolic solvent is selected from the group consisting of phenol, cresol, xylenol, propylphenol, butylphenol, amylphenol, octylphenol, nonylphenol, and mixtures thereof.

5. A process as claimed in claim 3 wherein said aromatic amine is admixed with a mixture of at least one of said isopropenyl phenol compounds and at least one phenolic solvent, said mixture being obtained by the alkali cleavage of bisphenol A.

6. A process as claimed in claim 3 wherein said phenolic solvent is present in an amount of 0.5 to 2 moles of phenol per mole of said isopropenyl phenol compound calculated as a monomer.

7. A process as claimed in claim 1 wherein said aromatic amine is admixed with a mixture of said isopropenyl phenol compound and a phenolic solvent, said mixture being obtained by the catalytic decomposition of a dihydroxydiaryl propane.

8. A process as claimed in claim 1 wherein at least two of said isopropenyl phenol compounds are reacted with said aromatic amine.

9. A process as claimed in claim 7 wherein said aromatic amine is aniline.

10. A process as claimed in claim 1 wherein said isopropenyl phenol compound is selected from the group consisting of p-isopropenyl phenol, di- to eicosa-mers of p-isopropenyl phenol, and mixtures thereof.

* * * * *